US00PP20485P2

(12) United States Plant Patent
Ui

(10) Patent No.: US PP20,485 P2
(45) Date of Patent: Nov. 17, 2009

(54) ***CALIBRACHOA* PLANT NAMED 'SAKCAL094'**

(50) Latin Name: ***Calibrachoa* sp.**
Varietal Denomination: SAKCAL094

(75) Inventor: Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/283,763

(22) Filed: Sep. 16, 2008

(51) Int. Cl.
*A01H 5/00* (2006.01)

(52) U.S. Cl. ..... Plt./413

(58) Field of Classification Search ..... Plt./413
See application file for complete search history.

*Primary Examiner*—Kent L Bell
(74) *Attorney, Agent, or Firm*—Jondle & Associates, P.C.

(57) ABSTRACT

'SAKCAL094' is a new *Calibrachoa* cultivar particularly distinguished by having large pink flowers and a creeping growth habit.

1 Drawing Sheet

Figure 1:
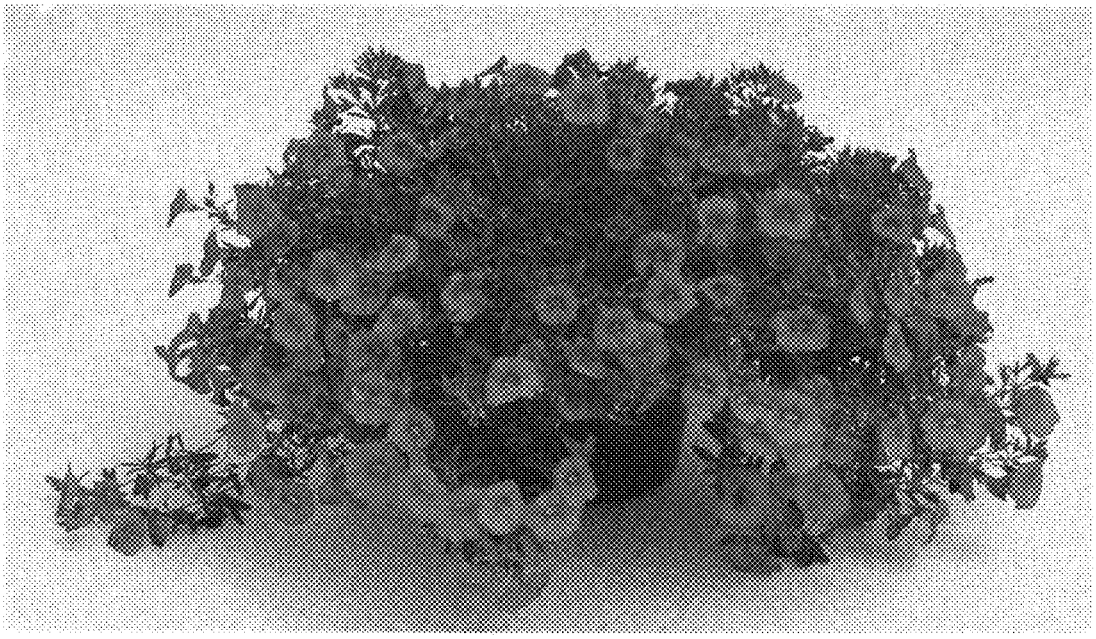

Genus and species: *Calibrachoa* sp.
Variety denomination: 'SAKCAL094'.

BACKGROUND OF THE INVENTION

The present invention comprises a new and distinct cultivar of *Calibrachoa*, botanically known as *Calibrachoa* sp., and hereinafter referred to by the cultivar name 'SAKCAL094.' It is characterized by having large pink flowers and a creeping plant growth habit. The new cultivar originated from a hybridization made in 2004 in Kakegawa, Japan. The female grand parent was a proprietary hybrid *Calibrachoa* breeding line named 'K9-326' having a pink flower color and a creeping plant growth habit. The male grandparent was a proprietary hybrid *Calibrachoa* breeding line named '1B-74A-1' characterized by its rose-pink flower color and creeping plant growth habit.

In November 2003, 'K9-326' and '1B-74A-1' were crossed and 200 seeds were obtained. In February 2004, the $F_1$ seed were sown in the greenhouse, cultivated and plant lines were produced with flower colors of Pink and Rose Pink and creeping plant growth habit. Three plant lines were selected within the $F_1$ plants that had large rose pink flowers and a creeping plant growth habit. The three plant lines were intercrossed and 1,050 seeds were obtained. The exact female and male parentage is unknown.

In July 2004, 600 seeds were sown in the greenhouse, cultivated and plant lines were produced with flower colors of rose-pink, pink and light pink and a creeping plant growth habit. The line 'K5-87' was selected for its pink flower color and creeping plant growth habit. In February 2005, line 'K5-87' was vegetatively propagated by cuttings, cultivated and evaluated.

'K5-87' was vegetatively propagated through several generations and was subsequently named 'SAKCAL094'. Its unique characteristics were found to reproduce true to type in successive generations of asexual propagation.

DESCRIPTION OF THE GENUS *CALIBRACHOA* LLAVE & LEX.

The genus *Petunia* was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

SUMMARY OF THE INVENTION

The following are the most outstanding and distinguishing characteristics of this new cultivar when grown under normal horticultural practices in Kakegawa, Japan.

1. Large pink flowers; and
2. Creeping plant growth habit.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

FIG. 1. shows overall plant habit.

Figure 2:
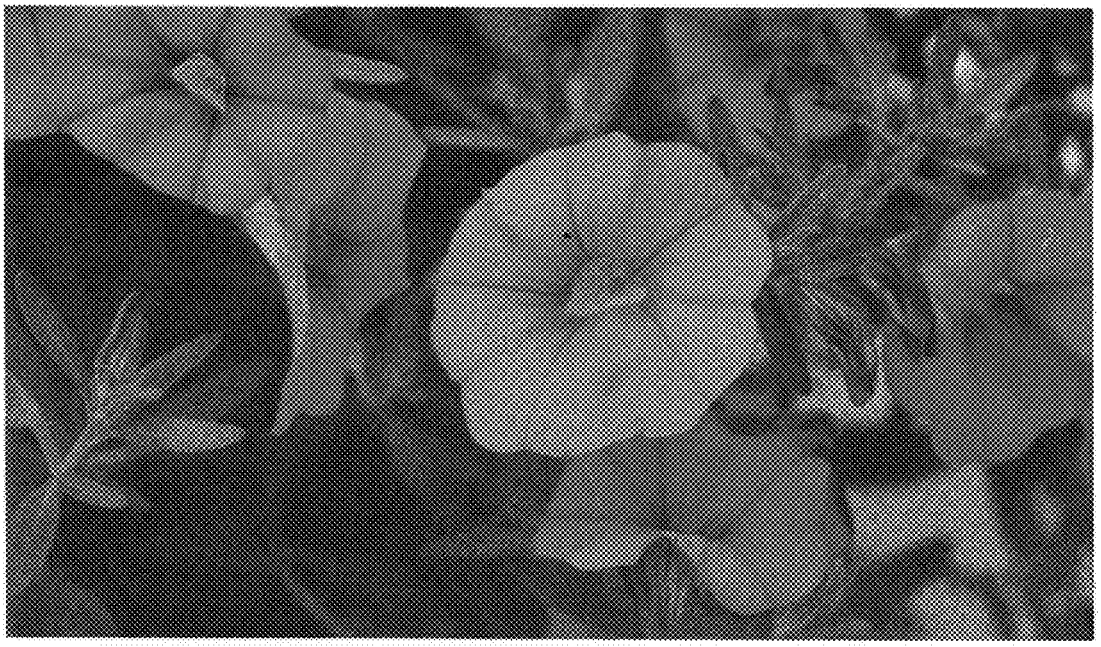

FIG. 2. shows the mature flowers.

DESCRIPTION OF THE NEW CULTIVAR

The following detailed description sets forth the distinctive characteristics of 'SAKCAL094'. The data which define these characteristics were collected from asexual reproductions carried out in Salinas, Calif. The detailed description was taken from plants grown under greenhouse conditions for approximately 4 months from transplanting of rooted cuttings. Color references are to The R.H.S. Colour Chart of The Royal Horticultural Society of London (R.H.S.), 4$^{th}$ Edition.

DETAILED BOTANICAL DESCRIPTION

Classification:

*Family.*—Solanaceae.

*Species.*—*Calibrachoa* sp. cultivar 'SAKCAL094'.

*Common name.*—*Calibrachoa.*

Plant description:

*Life cycle.*—Tender perennial.

*Form.*—Branching.

*Habit.*—Creeping.

*Height.*—10.0 cm to 12.0 cm from soil line to top of foliage.

*Spread.*—58.0 cm to 60.0 cm.

Propagation:

*Type cuttings.*—Vegetative cuttings.

*Time to produce a rooted cutting.*—6 weeks.

*Time to bloom from propagation.*—10 weeks.

Environmental conditions for plant growth: The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:

*Stem color.*—RHS 144C (Yellow-green).

*Anthocyanin color.*—Absent.

*Pubescence.*—Slight.

*Pubescence color.*—RHS N155A (White).

*Stem description.*—Dull, circular cross-section.

*Stem diameter.*—0.2 cm.

*Stem length.*—20.0 cm to 22.0 cm.

*Internode length.*—1.0 cm.

Leaves:

*Arrangement.*—Alternate.

*Shape.*—Elliptical.

*Apex.*—Obtuse.

*Base.*—Attenuate.

*Attachment.*—Decurrant.

*Margin.*—Entire.

*Surface appearance* (*both surfaces*).—Dull.

*Surface pubescence* (*both surfaces*).—Slight.

*Pubescence color.*—RHS N155A (White).

*Venation.*—Pinnate.

*Length.*—4.0 cm.

*Width.*—1.0 cm.

*Color.*—Upper surface: RHS 137B (Green). Lower surface: RHS 137C (Green).

*Fragrance.*—Absent.

*Petioles.*—Absent.

Flowers:

*Flowering habit.*—Indeterminate.

*Flower type.*—Solitary.

*Flowering requirements.*—Will flower so long as day length is greater than 12 hours and temperature exceeds 13° C.

*Duration of flowers.*—About 5 days.

*Corolla.*—5 petals, fused.

*Corolla shape.*—The flowers are funnel shaped with five fissures and a shallow, yet prominent, indentation of the petal tip at the midvein.

*Fragrance.*—Absent.

Flower buds:

*Texture.*—Pubescent.

*Length.*—2.0 cm to 2.5 cm.

*Diameter.*—0.5 cm to 0.8 cm.

*Shape.*—Ovate.

*Color.*—RHS N80A (Purple-violet) with RHS N79A (Purple) veins.

*Peduncle.*—Length: 1.5 cm to 2.0 cm. Diameter: 0.1 cm. Color: RHS 144C (Yellow-green). Texture: Dull appearance, moderate pubescence. Pubescence color: RHS N155A (White).

Flower description:

*Flower depth.*—1.0 cm.

*Flower diameter.*—4.0 cm.

*Flower tube length.*—1.5 cm to 2.0 cm.

*Flower tube diameter.*—0.5 cm to 0.7 cm.

*Petals.*—Shape: Bilabiate, fused; shallow, yet prominent indentation of the petal tip at the midvein. Petal size: Length: 2.0 cm. Width: 2.0 cm. Apex: Truncate. Margin: Entire. Texture: Glabrous. Color: Lobes: Upper surface: RHS N74A (Red-purple). Lower surface: RHS N74C (Red-purple) with RHS. N79A (Purple) veins. Corolla tube: Inner: RHS 11A (Yellow) with N79A (Purple) veins. Outer: RHS 10B (Yellow) with RHS N79A (Purple) veins.

*Calyx.*—5 sepals, free.

*Sepals.*—Shape: Elliptical. Apex: Obtuse. Margin: Entire. Sepal color (both surfaces): RHS 137C (Green).

*Fragrance.*—Absent.

Reproductive organs:

*Stamens.*—Number: 5, free. Color: RHS 154D (Yellow-green). Pollen color: RHS 11B (Yellow).

*Ovary.*—Superior.

*Placenta arrangement.*—Central.

*Pistil number.*—1 per flower.

*Pistil length.*—0.8 cm.

*Stigma color.*—RHS 144D (Yellow-green).

*Style length.*—0.6 cm.

*Style color.*—RHS 154D (Yellow-green).

Fruit/seed set: No fruit or seeds produced.

Disease and insect resistance: 'SAKCAL094' has excellent resistance to rain, heat and drought. It will not tolerate temperatures below 10° C. Plants are susceptible to *Botrytis,* powdery mildew, various stem and root rots, and certain viruses such as Tobacco Mosaic Virus and Impatiens Necrotic Spotted Virus. Plants can be infested with aphids, leafminer, whitefly and various *Lepidoptera.*

COMPARISON WITH PARENTAL LINES AND KNOWN CULTIVARS

'SAKCAL094' is distinguished from its grandparents mainly by flower color and plant growth habit as shown in Table 1 below.

TABLE 1

| Characteristic | 'SAKCAL094' | Female grandparent: 'K9-326' | Male grandparent: '1B-74A-1' |
|---|---|---|---|
| Flower color | Pink | Pink | Rose Pink |
| Plant growth habit | Creeping | Creeping | Creeping |

'SAKCAL094' is a distinct variety of large-flowered *Calibrachoa* owing to its pink flower color and creeping plant growth habit. 'SAKCAL094' is most similar to the variety 'USCALI11' (U.S. Plant Pat. No. 14,968); however, there are differences in flower petal color, flower size and plant growth habit as described in the table below:

TABLE 2

| Characteristic | 'SAKCAL094' | 'USCALI11' |
|---|---|---|
| Flower petal color, upper surface | RHS N74A (Red-Purple) | RHS 74B (Red-Purple) |
| Flower petal color, lower surface | RHS N74C (Red-Purple) with RHS N79A (Purple) veins | RHS 70B (Red-Purple) to RHS 70C (Red-Purple) |
| Flower size (diameter) | 4.0 cm | 2.9 cm |
| Plant growth habit | Creeping | Semi-upright |

I claim:

1. A new and distinct cultivar of *Calibrachoa* plant as shown and described herein.

* * * * *